United States Patent
Segawa (10) Patent No.: US 8,480,567 B2
(45) Date of Patent: Jul. 9, 2013

(54) ENDOSCOPE SYSTEM WITH DIFFERENTIAL SIGNAL TRANSMISSION

(75) Inventor: Kazunori Segawa, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 0 days.

(21) Appl. No.: 13/438,899

(22) Filed: Apr. 4, 2012

(65) Prior Publication Data

US 2012/0265012 A1    Oct. 18, 2012

Related U.S. Application Data

(63) Continuation of application No. PCT/JP2011/061095, filed on May 13, 2011.

(30) Foreign Application Priority Data

Jul. 30, 2010    (JP) .................................. 2010-172860

(51) Int. Cl.
*A61B 1/00*    (2006.01)

(52) U.S. Cl.
USPC .......................................... 600/134; 600/110

(58) Field of Classification Search
USPC .............. 600/134, 110; 348/65–76; 333/17.3, 333/32
See application file for complete search history.

(56) References Cited

U.S. PATENT DOCUMENTS

| | | | |
|---|---|---|---|
| 4,868,647 A | | 9/1989 | Uehara et al. |
| 6,459,447 B1 * | | 10/2002 | Okada et al. ..................... 348/65 |
| 6,503,103 B1 * | | 1/2003 | Cohen et al. ............. 439/607.09 |
| 7,821,530 B2 * | | 10/2010 | Amling et al. .................. 348/72 |
| 7,904,108 B2 * | | 3/2011 | Castaneda et al. ......... 455/550.1 |
| 8,411,138 B2 * | | 4/2013 | Tsuda et al. ..................... 348/65 |
| 2003/0042571 A1 | | 3/2003 | Chen et al. |
| 2004/0070468 A1 * | | 4/2004 | Harada ......................... 333/185 |
| 2006/0025651 A1 | | 2/2006 | Adler et al. |
| 2008/0025450 A1 | | 1/2008 | Alfano et al. |
| 2008/0136903 A1 * | | 6/2008 | Takada et al. ................... 348/65 |

(Continued)

FOREIGN PATENT DOCUMENTS

| | | |
|---|---|---|
| JP | 04-372213 | 12/1992 |
| JP | 10-211166 | 8/1998 |
| JP | 2007-167590 | 7/2007 |
| WO | WO 2007/004428 A1 | 1/2007 |

OTHER PUBLICATIONS

European Search Report dated Jan. 30, 2013 from corresponding European Patent Application No. EP 11 81 2142.5.

*Primary Examiner* — John P Leubecker (74) *Attorney, Agent, or Firm* — Scully, Scott, Murphy & Presser, P.C.

(57) ABSTRACT

An endoscope system includes: an LVDS driver that outputs a differential signal; a differential transmission line that transmits the differential signal outputted from the LVDS driver; a pulse transformer including, in order to input the differential signal transmitted by the differential transmission line, two input terminals connected to an end of the differential transmission line; a resistor functioning as a bypass impedance element connected on an input side of the pulse transformer, to which the differential signal is inputted, in parallel to the pulse transformer and having, at a predetermined noise frequency of noise mixed in the differential transmission line, impedance smaller than circuit impedance of a circuit to which the pulse transformer, which is connected in parallel to the bypass impedance element, is connected; and a dielectric disposed between the two input terminals of the pulse transformer and between lines of the differential transmission line.

7 Claims, 5 Drawing Sheets

U.S. PATENT DOCUMENTS

| | | |
|---|---|---|
| 2009/0028320 A1* | 1/2009 | Fuehrer et al. ........... 379/392.01 |
| 2009/0243028 A1 | 10/2009 | Dong et al. |
| 2009/0292169 A1* | 11/2009 | Mitani et al. .................. 600/110 |
| 2010/0026413 A1* | 2/2010 | Zabinski et al. ................ 333/32 |
| 2011/0212649 A1* | 9/2011 | Stokoe et al. ................ 439/626 |

* cited by examiner

ENDOSCOPE SYSTEM WITH DIFFERENTIAL SIGNAL TRANSMISSION

CROSS REFERENCE TO RELATED APPLICATION

This application is a continuation application of PCT/JP2011/061095 filed on May 13, 2011 and claims benefit of Japanese Application No. 2010-172860 filed in Japan on Jul. 30, 2010, the entire contents of which are incorporated herein by this reference.

BACKGROUND OF THE INVENTION

1. Field of the Invention

The present invention relates to an endoscope system and, more particularly, to an endoscope system using a pulse transformer to which a differential signal flowing through a differential signal line is inputted.

2. Description of the Related Art

Conventionally, endoscopes have been widely used in a medical field and an industrial field. In particular, in an endoscope system used in the medical field, in order to secure safety for patients, a part of a CCD driving circuit and a video signal processing circuit are mounted on a patient circuit insulated and separated from a secondary circuit.

For example, as disclosed in International Publication No. 2007/004428 and Japanese Patent Application Laid-Open Publication No. 2007-167590, an endoscope system that uses a differential signal for transmission of a signal between a patient circuit and a secondary circuit is proposed. In those proposals, the differential signal is a signal conforming to a standard of LVDS (Low Voltage Differential Signaling). For insulation, a pulse transformer is used in an LVDS transmission channel.

When external noise is mixed in a differential transmission line that transmits the differential signal, if the external noise is common mode noise, the external noise is cancelled by a subtraction in a termination circuit section. Therefore, the differential signal has a characteristic that the differential signal is robust against the external noise. Usually, a pattern on a substrate on an input side of the pulse transformer is formed such that characteristic impedance is, for example, 100 [Ω], and the common mode noise is cancelled.

SUMMARY OF THE INVENTION

According to an aspect of the present invention, it is possible to provide an endoscope system including: a driver that outputs a differential signal; a differential transmission line that transmits the differential signal outputted from the driver; a pulse transformer including, in order to input the differential signal transmitted by the differential transmission line, two input terminals connected to an end of the differential transmission line; an impedance member including a bypass impedance element connected on an input side of the pulse transformer, to which the differential signal is inputted, in parallel to at least the pulse transformer and having, at a predetermined noise frequency of noise mixed in the differential transmission line, impedance smaller than circuit impedance of a circuit to which the pulse transformer, which is connected in parallel to the bypass impedance element, is connected; and a dielectric disposed between the two input terminals of the pulse transformer and between lines of the differential transmission line such that a distance between the two input terminals of the pulse transformer is equal to inter-line impedance of the differential transmission line.

DETAILED DESCRIPTION OF THE PREFERRED EMBODIMENT

An embodiment of the present invention is explained below with reference to the drawings.

(Configuration of an Endoscope System)

Figure 1:
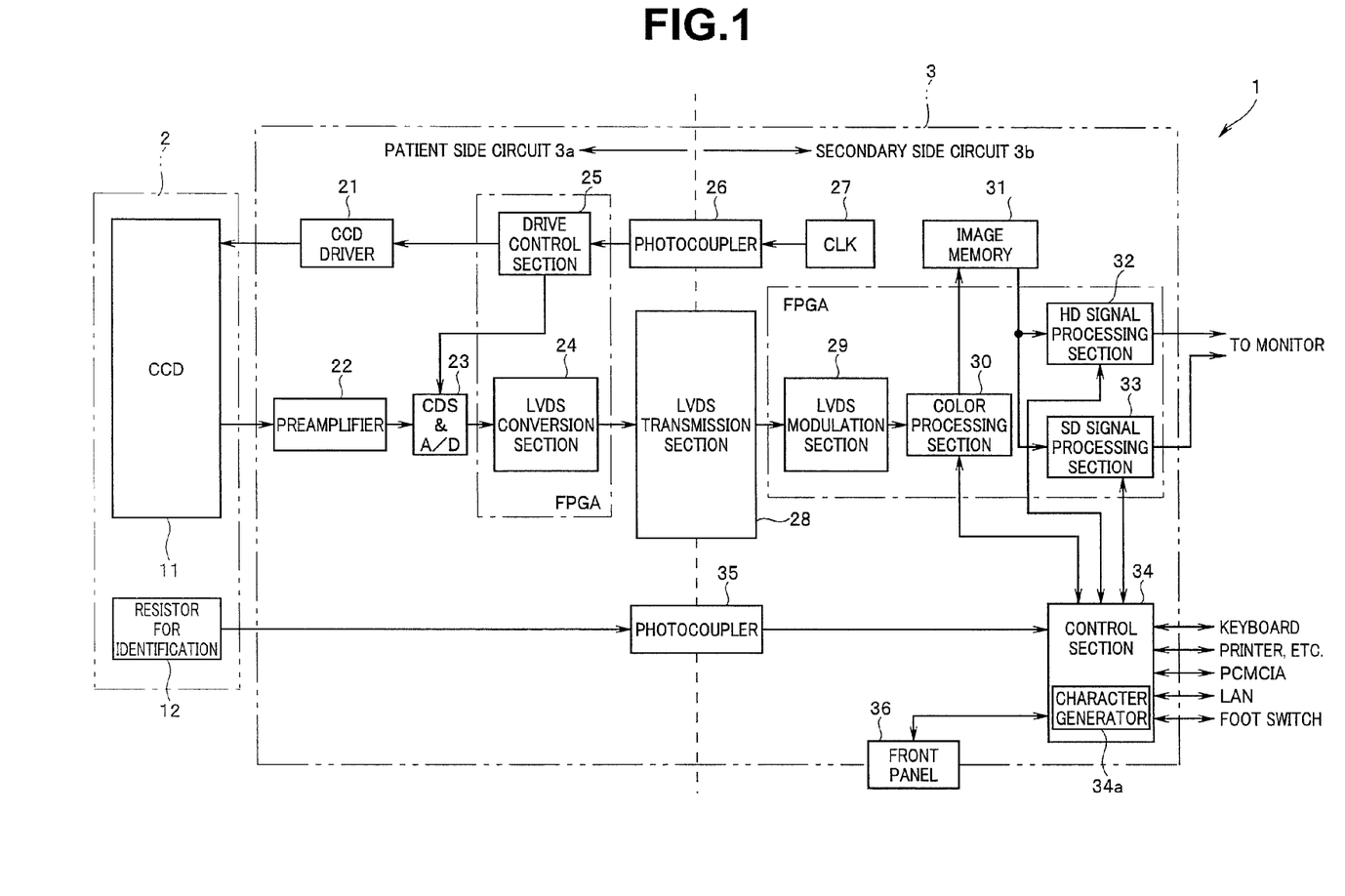
FIG. 1 is a configuration diagram showing a configuration of an endoscope system according to an embodiment of the present invention.

First, a configuration of an endoscope system according to the present embodiment is explained. FIG. 1 is a configuration diagram showing the configuration of the endoscope system according to the present embodiment.

As shown in FIG. 1, an endoscope system 1 includes an endoscope 2 and a processor 3 to which the endoscope 2 is connected and which performs, for example, signal processing for a video signal from an image pickup device. In the present embodiment, the endoscope 2 in the endoscope system 1 is an endoscope including an insertion section provided with the image pickup device at a distal end. However, the endoscope 2 may be a camera head mounted on a proximal end portion of a rigid endoscope.

The endoscope 2 includes a CCD 11 functioning as an image pickup device and a resistor for identification 12 of the endoscope 2. The endoscope 2 and the processor 3 are connected by a not-shown signal cable.

The processor 3 includes a patient side circuit 3a to which the endoscope 2 is connected and a secondary side circuit 3b electrically insulated from the patient side circuit 3a.

The patient side circuit 3a includes a CCD driver 21 that drives the CCD 11 of the endoscope 2, a preamplifier 22 that amplifies an image pickup signal from the endoscope 2, and a CDS & A/D section 23 that subjects the image pickup signal from the preamplifier 22 to correlated double sampling and digitizes the image pickup signal. The CDS & A/D section 23 converts the image pickup signal from the endoscope 2 inputted via the preamplifier 22 into a parallel signal having a predetermined frequency.

The parallel signal from the CDS & A/D section 23 is inputted to an LVDS conversion section 24. The LVDS conversion section 24 converts the inputted parallel signal into a serial signal for LVDS transmission.

The CCD driver 21 and the CDS & A/D section 23 are controlled by a drive control section 25. The drive control section 25 generates a CCD control signal on the basis of a reference clock from a clock circuit (CLK) 27 provided in the secondary side circuit 3b via a photocoupler 26 and controls the CCD driver 21 and the CDS & A/D section 23. The LVDS conversion section 24 and the drive control section 25 include FPGAs (field programmable gate arrays).

The serial signal for the LVDS transmission converted by the LVDS conversion section 24 is transmitted to an LVDS modulation section 29 of the secondary side circuit 3b via an LVDS transmission section 28.

The LVDS modulation section 29 subjects the serial signal inputted via the LVDS transmission section 28 to conversion opposite to the conversion performed by the LVDS conversion section 24 and converts the serial signal into a predetermined parallel signal. The converted parallel signal is subjected to color separation processing, synchronization processing, and the like by a color processing section 30 and stored in an image memory 31 as image data.

The image data stored in the image memory 31 is subjected to image signal processing by an HD signal processing section 32 or an SD signal processing section 33 and outputted to a not-shown monitor.

The color processing section 30, the HD signal processing section 32, or the SD signal processing section 33 are controlled by a control section 34. The control section 34 detects the resistor for identification 12 of the endoscope 2 via a photocoupler 35 to perform control of video processing corresponding to a type of the endoscope 2. The HD signal processing section 32 is a processing section that performs video signal processing at high resolution and the SD signal processing section 33 is a processing section that performs video signal processing at standard resolution. The LVDS modulation section 29, the color processing section 30, the HD signal processing section 32, and the SD signal processing section 33 include FPGAs (field programmable gate arrays).

The control section 34 includes an interface with not-shown peripheral apparatuses such as a keyboard, a printer, a PCMCIA, a LAN, and a foot switch and includes an interface with a front panel 36. Further, the control section 34 includes a character generator 34a on an inside. The control section 34 can generate a message corresponding to necessity and cause a monitor to display the message.

Figure 2:
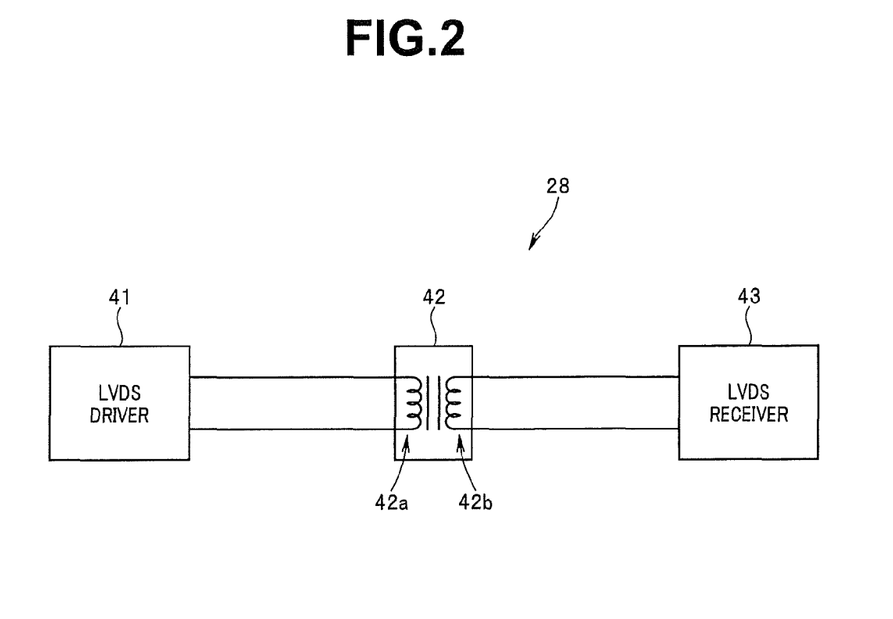
FIG. 2 is a configuration diagram showing a configuration of an LVDS transmission section 28 according to the embodiment of the present invention.

FIG. 2 is a configuration diagram showing a configuration of the LVDS transmission section 28. The LVDS transmission section 28 includes an LVDS driver 41, a pulse transformer 42, and an LVDS receiver 43.

The pulse transformer 42 includes a primary side coil 42a and a secondary side coil 42b. A serial signal from the LVDS conversion section 24 is inputted to the LVDS driver 41. The LVDS driver 41 is a driver that outputs a differential signal. The LVDS driver 41 supplies an LVDS signal to the coil 42a on an input side (i.e., the primary side) of the pulse transformer 42.

The coil 42b on an output side (i.e., the secondary side) of the pulse transformer 42 is connected to the LVDS receiver 43. The LVDS receiver 43 outputs the received LVDS signal to the LVDS modulation section 29.

(Connecting Structure of a Differential Transmission Line and the Pulse Transformer)

Figure 3:
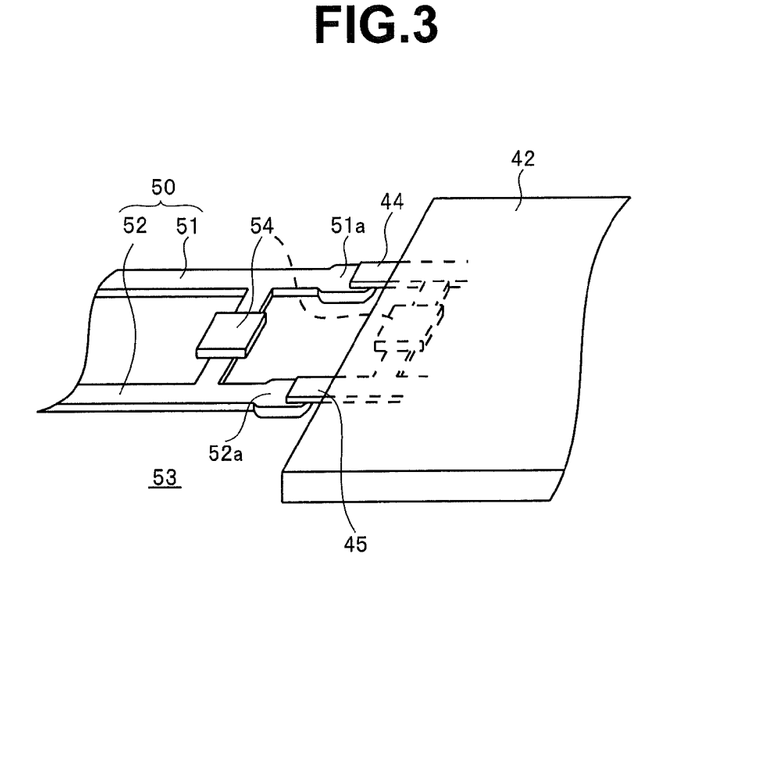
FIG. 3 is a perspective view of a connecting portion of a differential transmission line, which transmits an LVDS signal from an LVDS driver 41, and a pulse transformer 42 according to the embodiment of the present invention.

FIG. 3 is a perspective view of a connecting portion of a differential transmission line 50, which transmits an LVDS signal from the LVDS driver 41, and the pulse transformer 42.

As shown in FIG. 3, two wiring patterns (hereinafter referred to as differential patterns) 51, 52 forming the differential transmission line 50 are provided on a substrate 53. The differential transmission line 50 is a micro strip line that transmits a differential signal outputted from the LVDS driver 41. Further, the pulse transformer 42, which is a chip component, is also mounted on the substrate 53. The pulse transformer 42 is connected to an end of the differential transmission line 50. The differential signal transmitted by the differential transmission line 50 is inputted to the pulse transformer 42.

Two input terminals 44, 45 of the pulse transformer 42 are respectively connected to end portions (hereinafter referred to as connection end portions) 51a, 52a of the two differential patterns 51, 52 formed in parallel to each other. A distance between the two input terminals of the pulse transformer 42 is formed to be equal to inter-line impedance of the differential transmission line 50.

A resistor 54 to which the two differential patterns 51, 52 are connected is provided near the connection end portions 51a, 52a. The resistor 54, which is a chip component, is an impedance member that electrically connects the two input terminals 44, 45 of the pulse transformer 42, to which a differential signal is inputted, and has impedance smaller than impedance of the pulse transformer 42 at a predetermined noise frequency in noise mixed in the differential transmission line 50. In other words, the resistor 54 is an impedance member including a bypass impedance element connected in parallel to the pulse transformer 42. The impedance of the resistor 54 is smaller than circuit impedance on the pulse transformer 42 side connected in parallel to the resistor 54 at the predetermined noise frequency in the noise mixed in the differential transmission line 50.

As indicated by a dotted line in FIG. 3, the resistor 54 may be provided in the pulse transformer 42.

(Action)

Figure 4:
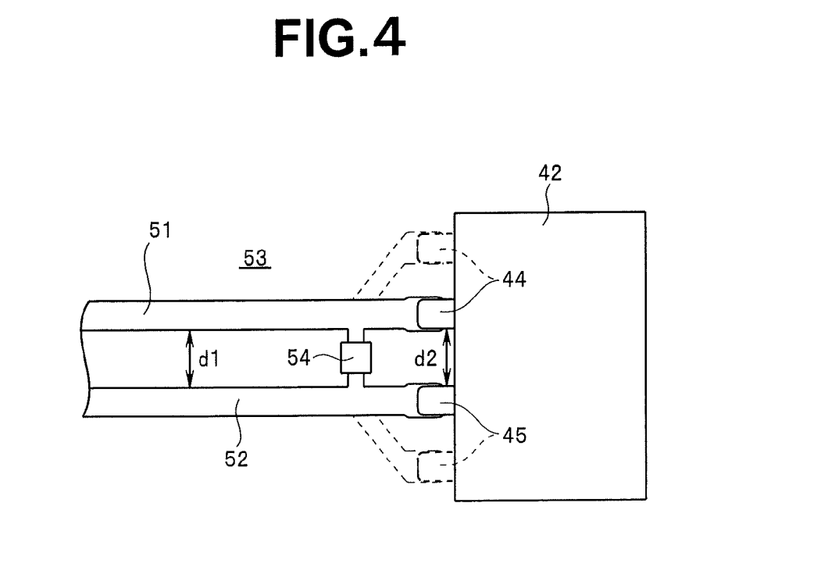
FIG. 4 is a diagram for explaining the connecting portion of the differential transmission line, which transmits the LVDS signal from the LVDS driver 41, and the pulse transformer 42 according to the embodiment of the present invention.
Figure 5:
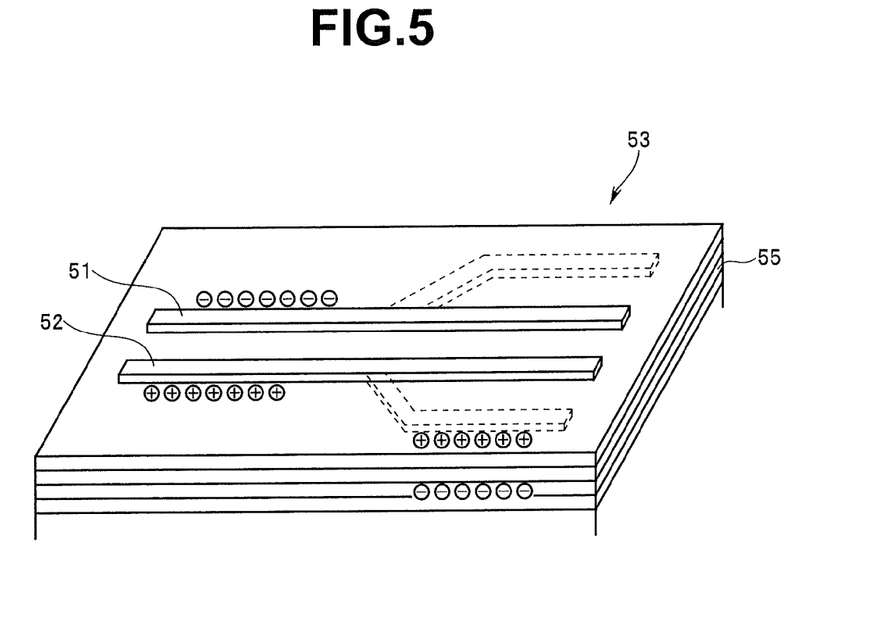
FIG. 5 is a diagram for explaining a flow of charges of a differential signal according to the embodiment of the present invention.

FIG. 4 is a diagram for explaining the connecting portion of the differential transmission line, which transmits the LVDS signal from the LVDS driver 41, and the pulse transformer 42. FIG. 5 is a diagram for explaining a flow of charges of a differential signal.

As shown in FIG. 5, the substrate 53 on which the differential transmission line 50 is provided is a multilayer substrate. The two differential patterns 51, 52 are formed on a top layer. A ground (GND) layer 55 is formed in the substrate 53.

Usually, the two differential patterns 51, 52 formed on the substrate 53 are designed while performing various simulations based on physical structures such as width of a pattern, thickness of an insulating layer, and a distance between the insulating layer and a ground (GND) and an inter-pair distance d1 between the two differential patterns 51, 52 is determined such that impedance of the differential transmission line 50 from a transmission position to a reception position of the differential signal is desired impedance.

In the present embodiment, as shown in FIGS. 3 and 4, the differential transmission line 50 and the pulse transformer 42 are connected such that the inter-pair distance d1 between the two differential patterns 51, 52 and a distance d2 between the two input terminals 44, 45 of the pulse transformer 42 are equal. In other words, the distance d2 between the two input terminals of the pulse transformer 42 is formed to be equal to the inter-line impedance of the differential transmission line 50.

This is to prevent impedance mismatch from occurring in the connecting portion of the differential transmission line 50 and the pulse transformer 42.

This point is specifically explained. It is assumed that the differential transmission line 50 and the pulse transformer 42 are connected such that the distance between the two input terminals 44, 45 of the pulse transformer 42 and the inter-pair distance between the two differential patterns 51, 52 are different. For example, as indicated by a dotted line in FIG. 4, it is assumed that the inter-pair distance between the two differential patterns 51, 52 increases toward the connection end portions 51a, 52a.

When positive charges of a P channel flow to the differential pattern 52, negative charges are excited in an N channel and flow to the differential pattern 51. Between the two differential patterns 51, 52 in which the inter-pair distance d1 determined by design is kept, since magnetic fields generated in the two differential patterns 51, 52 are in opposed directions, radiation of noise does not occur.

However, as indicated by dotted lines in FIGS. 4 and 5, when the distance d2 between the connection end portions 51a, 52a of the differential patterns 51, 52 is larger than the inter-pair distance d1, the differential patterns 51, 52 are formed to expand toward the connection end portions 51a, 52a. Mismatch of impedance occurs in a portion where the distance between the differential patterns expands.

As the distance between the patterns expands, in some case, the negative charges corresponding to the positive charges flowing to the differential pattern 52 do not flow to the differential pattern 51 and are generated and flow to the ground (GND) layer 55 closer from the differential pattern 52 than the differential pattern 51. In that case, a leak of the negative charges occurs in the ground (GND) layer and radiation from the ground (GND) layer 55 occurs. Since the mismatch of impedance occurs, the differential patterns 51, 52 are easily affected by noise from an outside.

Therefore, as indicated by solid lines in FIGS. 3 to 5, the inter-pair distance d1 between the differential patterns 51, 52 are kept up to the connection terminal sections 51a, 52a. To keep the inter-pair distance d1, the distance d2 between the input terminals 44, 45 of the pulse transformer 42 is set equal to the inter-pair distance d1.

Instead of fixing the inter-pair distance between the differential patterns 51, 52, in a region expanding toward the connection end portions 51a, 52a in the differential patterns 51, 52, a dielectric may be provided to set the distance between the two input terminals of the pulse transformer 42 equal to the inter-line impedance of the differential transmission line 50.

Figure 6:
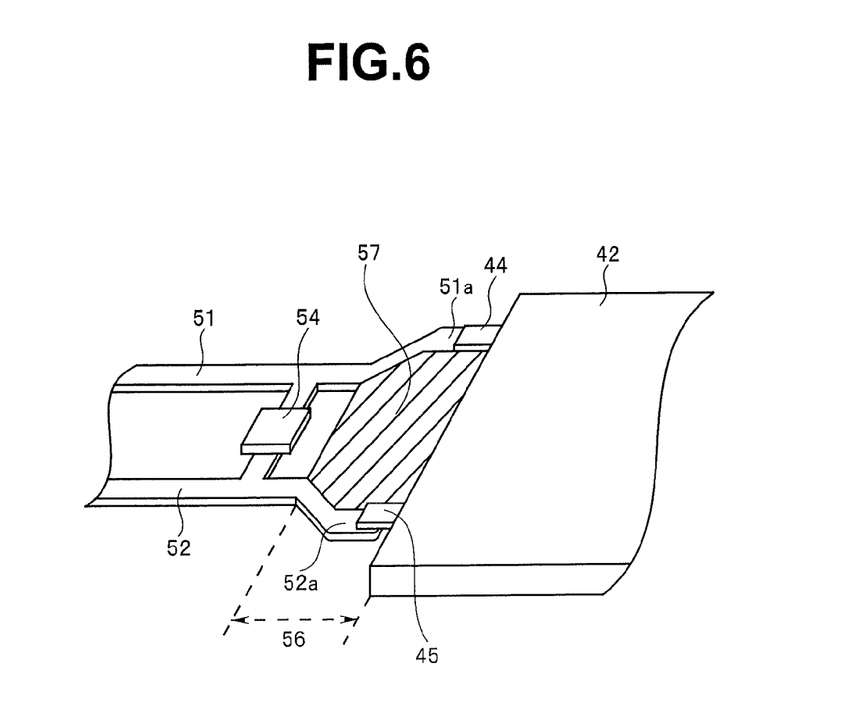
FIG. 6 is a diagram showing a state in which a dielectric member is provided between connection end portions 51a, 52a of differential patterns 51, 52 according to the embodiment of the present invention.

FIG. 6 is a diagram showing a state in which a dielectric member is provided between the connection end portions 51a, 52a of the differential patterns 51, 52. As shown in FIG. 6, a dielectric member 57 is provided in a region 56 between patterns expanding toward the connection end portions 51a, 52a in the pair of differential patterns 51, 52.

A dielectric constant $\in 2$ of the dielectric member 57 provided in the region 56 is a value at which the distance between the patterns in the expanding portion is seemingly the same as the inter-pair distance d1 of the differential pattern 50. The dielectric constant $\in 2$ is larger than a dielectric constant $\in 1$ between the patterns in a region where the differential patterns 51, 52 are parallel. As a material of the dielectric, for example, there is a ceramic material having a dielectric constant higher than a dielectric constant of an epoxy material in a normal region.

Next, action of the resistor 54 is explained.

Figure 7:
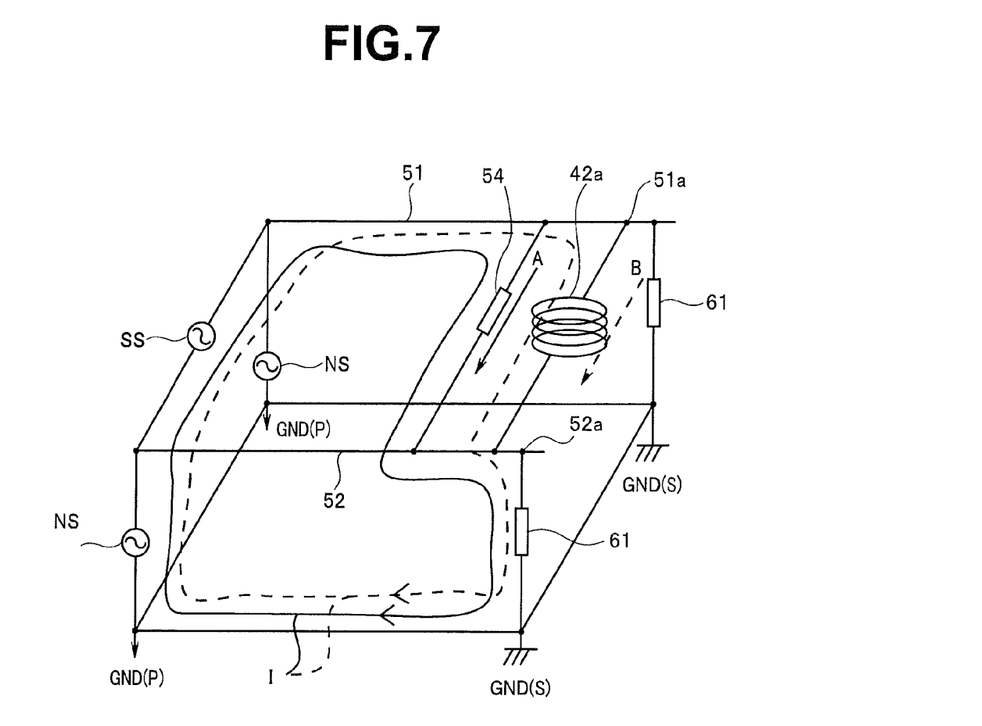
FIG. 7 is a circuit diagram for explaining action of a resistor 54 according to the embodiment of the present invention.

FIG. 7 is a circuit diagram for explaining the action of the resistor 54. As shown in FIG. 7, an LVDS signal source SS corresponding to the LVDS driver 41 is connected between the differential patterns 51, 52. The coil 42a corresponding to primary winding in the pulse transformer 42 is connected between the connection end portions 51a, 52a of the differential patterns 51, 52. Further, the resistor 54 connected in parallel to the coil 42a is connected between the differential patterns 51, 52. Impedance Z of the pulse transformer 42 including the coil 42a is different according to a frequency of a signal.

In FIG. 7, noise due to static electricity, an electric knife, or the like is shown as a noise source NS connected between each of the differential patterns 51, 52 and a substrate ground (GND(P)) of the patient side circuit 3a. Further, impedance Z0 between the differential patterns 51, 52 and the ground layer (GND(S)) 55 is shown as an impedance element 61.

When noise is mixed in the differential transmission line 50, the impedance of the pulse transformer 42 changes to impedance corresponding to a frequency of the noise. For example, when a frequency of a noise signal is 30 [MHz] and the coil 42a has 50 [μH], impedance Z of the pulse transformer 42 including the coil 42a is 95 kΩ (=50×(2×π×300)).

On the other hand, impedance Z1 of the resistor 54 is selected to be smaller than the impedance Z of the pulse transformer 42 at a predetermined frequency of noise mixed in the differential patterns 51, 52.

For example, the impedance Z0 of the impedance element 61 (i.e., between the differential patterns 51, 52 and the ground (GND(S)) layer 55) is high impedance, for example, 30 [kΩ]. The impedance Z1 of the resistor 54 is low impedance, for example, 100 [Ω].

The impedance Z1 of the resistor 54 is selected to be larger than the impedance Z of the pulse transformer 42 at a frequency of a differential signal of LVDS to be transmitted. Consequently, an electric current of the differential signal flows to the coil 42a of the pulse transformer 42.

However, when a noise signal is mixed in the differential patterns 51, 52, the impedance Z1 of the resistor 54 at the noise frequency of the noise of the electric knife or the like is smaller than the impedance Z2 of the coil 42a. In the example explained above, the impedance Z1 of the resistor 54 is 100Ω and the impedance Z of the pulse transformer 42 is 15 kΩ. Therefore, an electric current I including a noise current In does not flow to the coil 42a and flows to the resistor 54 having the low impedance.

In FIG. 7, a solid line indicates a case in which the electric current I including the noise current In flows to the resistor 54 in a direction indicated by an arrow A of the slid line. A dotted line indicates a case in which the electric current I including the noise current In flows to the coil 42a in a direction indicated by an arrow B of the dotted line.

When the noise having the predetermined frequency is mixed, compared with a potential difference (I×15 kΩ) between both ends of the coil 42a in the case in which the electric current I flows to the coil 42a, a potential difference (I×100Ω) between both the ends of the coil 42a in the case in which the electric current I flows to the resistor 54 is low. Therefore, deterioration in a differential signal, which is an actual signal, is substantially suppressed.

In other words, since most of the electric current I flows to the resistor 54 connected in parallel to the coil 42a, it is possible to substantially suppress deterioration in the actual signal on the differential patterns 51, 52 due to the noise current In.

Therefore, it is possible to suppress the deterioration in the actual signal during mixing of noise by setting, on the basis of the frequency of the noise due to the static electricity, the electric knife, or the like, the impedance of the pulse transformer 42 and the impedance of the resistor 54 in the relation described above. As a result, according to the embodiment explained above, it is possible to realize an endoscope system having improved immunity tolerance.

In the embodiment explained above, as an example of the impedance member, the resistor, which is a passive component, having the impedance smaller than the impedance of the pulse transformer at the predetermined noise frequency of the noise mixed in the differential pattern is explained. However, instead of the resistor, a capacitor or a coil may be used as the passive component as long as the capacitor or the coil has such impedance. Further, the passive component may be a passive component including a combination of two or more components selected out of the resistor, the capacitor, and the coil. In other words, the impedance member may be a passive component including at least one of the resistor, the capacitor, and the coil.

Figure 8:
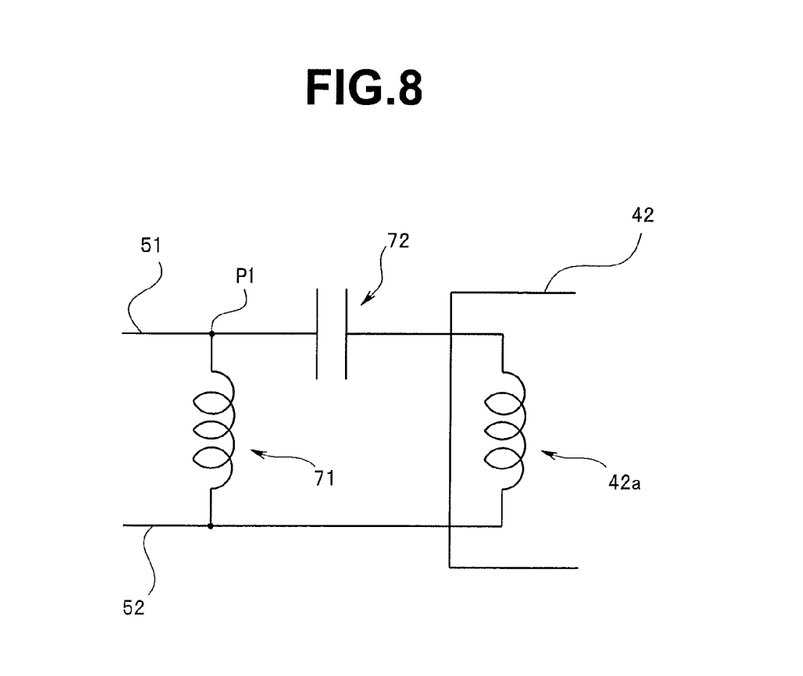
FIG. 8 is a diagram showing an example of a circuit in a case in which a circuit including a capacitor and a coil is used as an impedance member.

FIG. 8 is a diagram showing an example of a circuit in a case in which a circuit including a capacitor and a coil is used as the impedance member.

As shown in FIG. 8, a coil 71 functioning as a bypass impedance element is connected between the differential patterns 51, 52. A capacitor 72 is connected between a connection point P1 of the coil 71 and the differential pattern 51 and one end of the coil 42*a*.

For example, it is assumed that a noise frequency is 10 MHz, a frequency of a differential signal is 300 MHz, an inductor of the coil 71 functioning as the bypass impedance element is 200 µH, capacitance of the capacitor 72 is 0.1 pF, and impedance between a differential pattern and a ground (GND(S)) layer is 1 MΩ.

In this case, at the noise frequency (10 MHz), whereas impedance of the coil 71 is 12 kΩ, a sum of impedance on a pulse transformer side and impedance of the capacitor is 162 kΩ.

On the other hand, at the signal frequency (300 MHz), whereas a sum of impedance on the pulse transformer side and impedance of the capacitor is 99 kΩ, impedance of the coil 71 is 376 kΩ. Further, as explained above, the impedance between the differential pattern and the ground (GND(S)) layer is 1 MΩ.

Therefore, at the signal frequency (300 MHz), the sum of the impedance on the pulse transformer side and the impedance of the capacitor 72 is smaller than the impedance of the coil 71. Therefore, a signal current flows to the pulse transformer 42. On the other hand, at the noise frequency (10 MHz), the impedance of the coil 71 is smaller than the sum of the impedance on the pulse transformer side and the impedance of the capacitor 72. Therefore, a noise current does not flow to the pulse transformer 42 and flows to the coil 71.

As explained above, in the case of FIG. 8, at the noise frequency, the impedance of the coil 71 functioning as the bypass impedance element is smaller than impedance of a circuit (a circuit including the capacitor 72 and the coil 42*a*) connected in parallel to the coil 71. As a result, the noise current flows to the coil 71 functioning as the bypass impedance element. However, a differential signal current flows to a circuit on the pulse transformer side.

Furthermore, in the embodiment explained above, an example in which the differential signal is the LVDS signal is explained. However, the configuration of the embodiment explained above is also applicable to differential signals of RS-422, DVI, eDP, V-by-One Hs, and the like.

In the embodiment explained above, an example of the differential signal flowing to the patterns provided on the substrate is explained. However, a technique of the embodiment explained above can also be applied to a differential signal flowing to a twist pair line.

As explained above, with the endoscope system according to the embodiment explained above, when the differential signal is transmitted via the pulse transformer, it is possible to suppress deterioration in the actual signal of the differential signal using the impedance member having impedance smaller than the impedance of the pulse transformer at the noise frequency between lines of the differential transmission line.

In the past, in some case, impedance due to an inductance component between the terminals of the primary side coil in the pulse transformer is high depending on a frequency of noise. Therefore, there is a problem in that, when external noise of static electricity, an electric knife, or the like flows to the primary side coil, a large potential difference occurs between both ends of the primary side coil and the actual signal in the differential signal is deteriorated. However, according to the embodiment explained above, it is possible to realize an endoscope system having improved immunity tolerance.

Therefore, according to the embodiment explained above, it is possible to realize an endoscope system having improved immunity tolerance.

The present invention is not limited to the embodiment explained above. Various changes, modifications, and the like are possible in a range in which the spirit of the present invention is not changed.

What is claimed is:

1. An endoscope system comprising:
   a driver that outputs a differential signal;
   a differential transmission line that transmits the differential signal outputted from the driver;
   a pulse transformer including, in order to input the differential signal transmitted by the differential transmission line, two input terminals connected to an end of the differential transmission line;
   an impedance member including a bypass impedance element connected on an input side of the pulse transformer, to which the differential signal is inputted, in parallel to at least the pulse transformer and having, at a predetermined noise frequency of noise mixed in the differential transmission line, impedance smaller than circuit impedance of a circuit to which the pulse transformer, which is connected in parallel to the bypass impedance element, is connected; and
   a dielectric disposed between the two input terminals of the pulse transformer and between lines of the differential transmission line such that a distance between the two input terminals of the pulse transformer is equal to inter-line impedance of the differential transmission line.

2. The endoscope system according to claim 1, wherein the impedance member is a passive component including at least one of a resistor, a capacitor, and a coil.

3. The endoscope system according to claim 1, wherein, at a frequency of the differential signal to be transmitted, the impedance of the bypass impedance element is larger than the circuit impedance of the circuit to which the pulse transformer, which is connected in parallel to the bypass impedance element, is connected.

4. The endoscope system according to claim 1, wherein the differential signal line is a differential pattern provided on a substrate.

5. The endoscope system according to claim 4, wherein, in the differential pattern, the dielectric is provided in a region between patterns expanding toward connection end portions for connection to the pulse transformer.

6. The endoscope system according to claim 1, wherein the differential signal line is a twist pair line.

7. The endoscope system according to claim 1, wherein the impedance member is a coil, and
a capacitor is connected between a connection point of the coil and one line of the differential transmission line and one end of the pulse transformer.

* * * * *